United States Patent [19]
Biedermann

[11] Patent Number: 6,030,418
[45] Date of Patent: Feb. 29, 2000

[54] BLANK FOR PRODUCING A SOFT WALL INSIDE SOCKET

[75] Inventor: Lutz Biedermann, VS-Villingen, Germany

[73] Assignee: Biedermann Motech GmbH, Germany

[21] Appl. No.: 09/068,149

[22] PCT Filed: Sep. 17, 1997

[86] PCT No.: PCT/EP97/05099

§ 371 Date: May 13, 1998

§ 102(e) Date: May 13, 1998

[87] PCT Pub. No.: WO98/11849

PCT Pub. Date: Mar. 26, 1998

[30] Foreign Application Priority Data

Sep. 17, 1996 [DE] Germany .......................... 196 37 937

[51] Int. Cl.[7] ................................. A61F 2/80; A61F 2/60
[52] U.S. Cl. .............................................. 623/36; 623/33
[58] Field of Search .............................. 623/36, 33, 27, 623/34, 35, 37, 38

[56] References Cited

U.S. PATENT DOCUMENTS

| | | | |
|---|---|---|---|
| 2,025,835 | 12/1935 | Trautman | 623/36 |
| 3,309,714 | 3/1967 | Porten | 3/20 |
| 3,600,717 | 8/1971 | McKeehan | 3/19 |
| 4,274,166 | 6/1981 | Chambers | 3/17 |
| 4,479,272 | 10/1984 | Beldzisky | 623/36 |
| 4,635,626 | 1/1987 | Lerman | 128/165 |
| 5,480,455 | 1/1996 | Norvell | 623/36 |

FOREIGN PATENT DOCUMENTS

| | | | |
|---|---|---|---|
| 2 345 139 | 10/1977 | France . | |
| 331 517 | 1/1921 | Germany . | |
| 9427526 | 12/1994 | WIPO | 623/36 |

*Primary Examiner*—Mickey Yu
*Assistant Examiner*—Alvin Stewart
*Attorney, Agent, or Firm*—George W. Neunner; Dike, Bronstein, Roberts & Cushman, LLP

[57] ABSTRACT

A blank is described for producing a soft wall inside socket of a prosthesis having a pre-shaped side wall formed of a thermoplastic material, an inside liner and an outside sheathing. The blank forms a receiving space for receiving a shank stump and having an opening restricted by an edge of said side wall, for inserting the shank stump. For the purpose of adapting the height of said edge of the blank to the shank stump to be received, a slit-shaped recess runs along said edge and extends from the edge into the side wall by a predetermined depth (T). Preferably, the slit-shaped recess is arranged in the center of the side wall such that a double wall portion is formed with an inner wall adjacent to the inner liner and an outer wall adjacent to the outer sheathing, whereby the thickness of the inner wall essentially corresponds to the thickness of the outer wall.

9 Claims, 2 Drawing Sheets

BLANK FOR PRODUCING A SOFT WALL INSIDE SOCKET

BACKGROUND OF THE INVENTION

The present invention relates to a blank for producing a soft wall inside socket of a prosthesis comprising a pre-shaped side wall formed of a thermoplastic material, an inside liner and an outside sheathing, the blank forming a receiving space for receiving a shank stump or lower leg stump, having an opening restricted by an edge of the side wall for inserting the shank stump.

Such a blank is known from the U.S. Pat. No. 4,635,626.

A blank for a soft wall inside socket is known consisting of a thermoplastic material. The blank is pre-shaped such that it forms a receiving space having an opening restricted by an edge for receiving a shank stump. On the inner side of the receiving space a liner is provided made of body compatible material. At the outer side a sheathing of wear resistant material is deposited. The liner and the sheathing are sewn to each other at the edge of the opening such that the edge is formed rounded. For individually adapting the blank to a shank stump of an amputee the blank is heated to about 80° C. The blank is pushed onto the shank stump and applied with excess pressure in a known manner. Thereby, the blank is precisely adapted to the individual shank stump. After cooling of the blank it keeps its form so that the soft wall inside socket is completed.

The above-described blank has the disadvantage that in a normally necessary adaption of its length along the shank stump the edge cannot be perfectly closed because of the thickness of the thermoplastic material, which can lead to substantial drawbacks during wearing.

SUMMARY OF THE INVENTION

It is the object of the invention to provide a blank of a thermoplastic material for producing a soft wall inner socket which can be individually adapted in the length, and the edge of the receiving opening of which can be individually cut and formed rounded.

According to the invention a blank is provided for producing a soft wall inside socket of a prosthesis comprising a pre-shaped side wall formed of a thermoplastic material, an inside liner and an outside sheathing, the blank forming a receiving space for receiving a shank stump, having an opening restricted by an edge of the side wall, for inserting the shank stump, wherein, for the purpose of adapting the height of the edge of the blank to the shank stump to be received, a slit-shaped recess runs along the edge and extends from the edge into the side wall by a predetermined depth.

By providing the slit-shaped recess it is possible to adapt the height of the edge to the individual shank stump and to connect thereafter the liner with the sheathing.

The invention also provides a blank wherein the slit-shaped recess is arranged in the center of the side wall such that a double wall portion is formed with an inner wall adjacent to the inner liner and an outer wall adjacent to the outer sheathing, whereby the thickness of the inner wall essentially corresponds to the thickness of the outer wall. Preferably the side wall is formed integrally and the material is a thermoplastic foam material. Generally, the depth (T) of the slit-shaped recess is about 2 to 4 cm and the width (B) is about ⅓ to ½ of the thickness (D) of the side wall.

A soft wall inside socket is formed of a blank, as described above, such that the height of the soft wall inside socket is adapted to the shank stump by cutting off a portion of the side wall, of the outer sheathing and of the inner liner, and that thereafter the outer sheathing is connected with the inner liner. Preferably, the soft wall inside socket is adapted to the shank stump by cutting such that the outer sheathing and an outer wall portion, which is between the slit-shaped recess and the outer sheathing, are shortened more than the inner liner and an inner wall portion, which is between the slit-shaped recess and the inner liner, are shortened.

Further features and advantages of the invention will be apparent from the description of embodiments with reference to the figures.

DESCRIPTION OF THE INVENTION INCLUDING PREFERRED EMBODIMENTS

Figure 1:
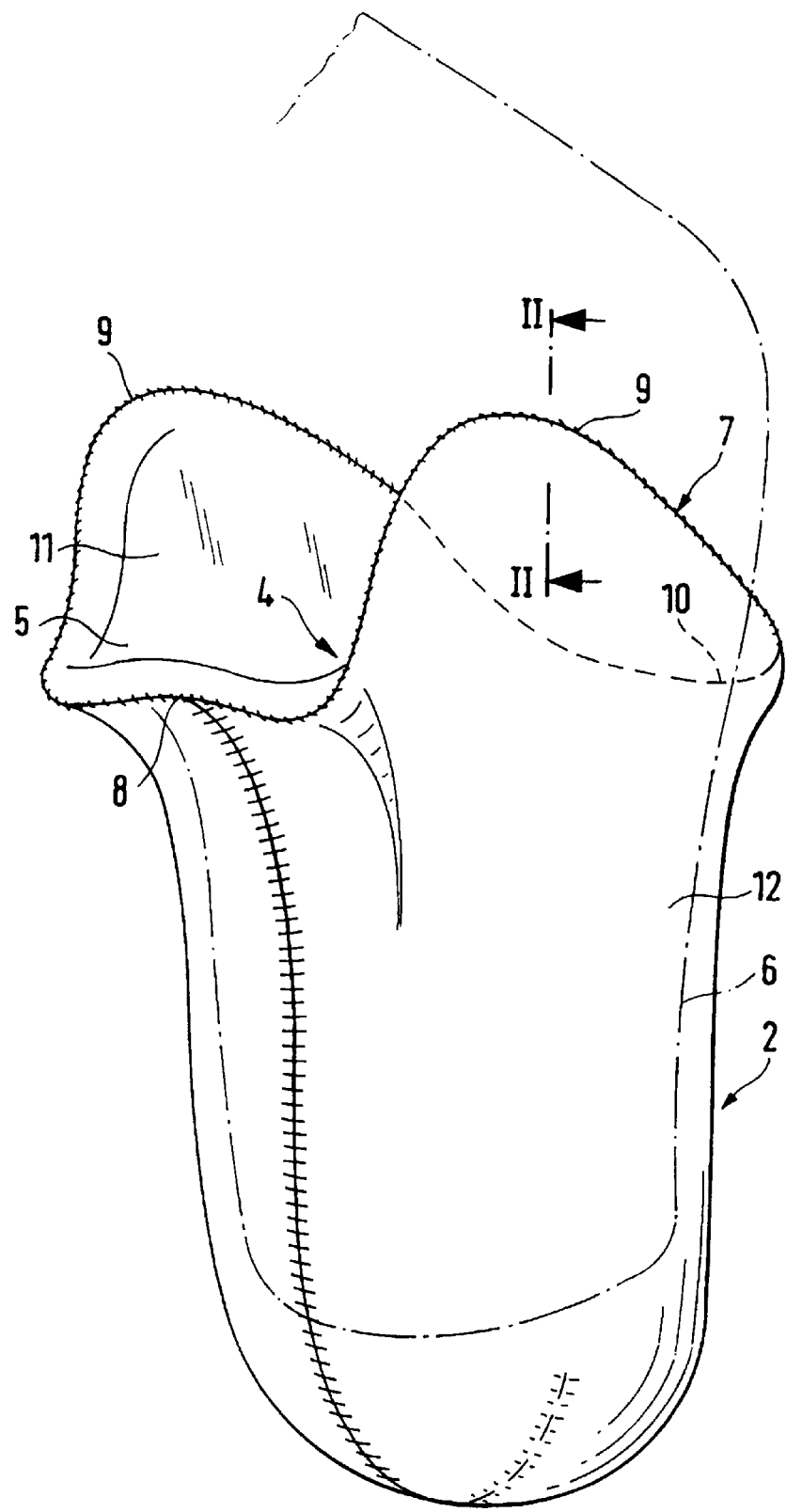
FIG. 1 is a perspective view of a soft wall inner socket produced from a blank.

As can be seen from the figures, the blank 1 for a soft wall inner socket 2 comprises a side wall 3 pre-shaped of a thermoplastic foam material with a thickness D, being preferably in the order of magnitude of 4 to 8 mm. The integral side wall 3 forms a receiving space 4 having a receiving opening 5 for receiving a shank stump 6. The side wall 3 is pre-shaped such that the shank stump 6 to be received is surrounded. The receiving opening 5 is restricted by an edge 7. The run of the edge is adapted to a popliteal space of a shank stump amputee, and it comprises a back portion 8 which contacts the popliteal space of the amputee during use. To the back portion 8 on both sides each a side portion 9 is connected therewith which runs in an arcuate shape, as is shown in FIG. 1, and sits close at the side of the knee during use. Both of the side portions 9 are connected by a front portion 10 which sits close below the patella.

Figure 2:
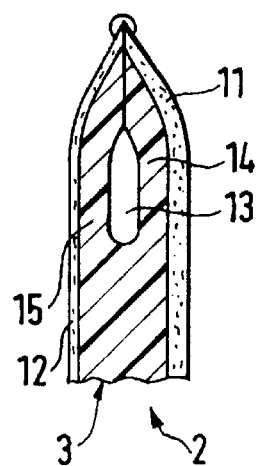
FIG. 2 is a schematical side view along the line II/II in FIG. 1.
Figure 2A:
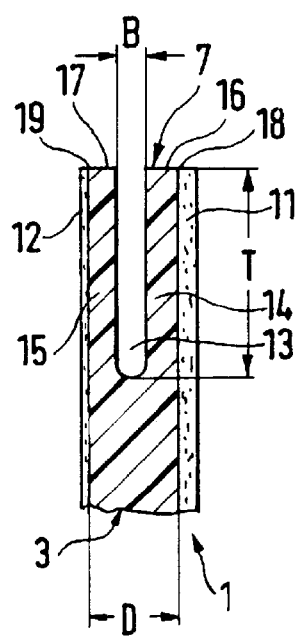
FIG. 2a is the side view of FIG. 2 of the blank before the soft wall inside socket is formed.

As can be seen in particular from FIGS. 2 and 2a, on the inside of the blank 1 an inside liner 11 is provided which is formed of a body compatible material. On the outside of the blank 1 an outer sheathing 12 of wear resistant material is provided.

As is shown in FIG. 2a, a slit-shaped recess 13 is provided in the edge 7 of the side wall 3 which extends around the whole edge 7 with a depth T of preferably 25 to 50 mm or 30 to 40 mm into the side wall 3. The slit-shaped recess 13 comprises a width B of about ⅓ to ½ of the thickness D of the side wall 3. Because of the slit-shaped recess 13 the side wall 3 comprises a double wall portion at at the edge portion having an inner wall 14 and an outer wall 15 in parallel thereto, which is formed in a U-shaped cross-section. The slit-shaped recess 13 is arranged in the center of the side wall 3 such that a thickness of the inner wall 14 corresponds essentially to a thickness of the outer wall 15. The inner wall 14 comprises at the edge 7 a first front face 16 adjacent to the inner liner 11 and the slit-shaped recess 13, and the outer wall 15 comprises a second front face 17 at the edge 7 adjacent to the outer sheathing 12 and the slit-shaped recess 13. The first front face 16 comprises a first edge 18 adjacent to the inner liner 11, and the second front face 17 comprises a second edge 19 adjacent to the outer sheathing 12. Due to the dimensions of the slit-shaped recess 13 the first edge 18 can be brought easily in contact with the second edge 19.

For adapting the blank 1 to a shank stump 6 of an amputee the blank 1 is heated to about 80° C. At this temperature, the thermoplastic foam material can be shaped. The thus heated blank 1 is pushed over the shank stump 6 of the amputee and is applied from the outside with excess pressure. Thereby, the blank 1 is adapted to the precise form of the shank stump 6. After the blank 1 is cooled, it maintains its shape. Thereafter, the height of the edge is adapted by cutting off the portions of the edge 7 which are too high. To this purpose, the blank 1 is taken off, and the first and second edges 18 and 19, respectively, of the inner liner 11 and the outer sheathing 12 are brought into contact, and the inner liner 11 and the outer sheathing 12 are sewn with each other such that a rounded edge is formed. As an alternative, the inner liner 11 and the outer sheathing 12 and the inner and outer walls 14, 15 may be bound by adhesive.

In a further embodiment, the outer wall 15 is shortened with the outer sheathing 12 in a higher amount than the inner wall 14 with the inner liner 11 so that the sewn or adhesively bound edge 7 is inclined to the outside as is shown in FIG. 1. Thereby, dressing and wearing of the soft wall inner socket 2 is facilitated.

What is claimed:

1. A blank for producing a soft wall inside socket of a prosthesis comprising a pre-shaped side wall formed of a thermoplastic material, an inside liner and an outside sheathing, said blank forming a receiving space for receiving a shank stump and having a shank stump receiving opening restricted by an edge of said side wall, for inserting said shank stump, wherein, for the purpose of adapting the height of said edge of said blank to said shank stump to be received, a slit-shaped recess is arranged in said side wall and runs along said edge and extends from said edge into said side wall by a predetermined depth (T).

2. The blank according to claim 1, wherein the side wall is formed integrally.

3. The blank according to claim 1, wherein the material is a thermoplastic foam material.

4. A method of producing a soft wall inside socket from a blank of one of claims 1, 2, or 3 wherein the height of the soft wall inside socket is adapted to the shank stump by cutting off a portion of the side wall, of the outer sheathing and of the inner liner, and that thereafter the outer sheathing is connected with the inner liner.

5. The method of claim 4, wherein said adaptation to the shank stump includes cutting such that the outer sheathing and an outer wall portion, which is between the slit-shaped recess and the outer sheathing, are shortened more than the inner liner and an inner wall portion, which is between the slit-shaped recess and the inner liner, are shortened.

6. A soft wall inside socket which is produced by the method of claim 4.

7. A soft wall inside socket which is produced by the method of claim 5.

8. A blank for producing a soft wall inside socket of a prosthesis comprising a pre-shaped side wall formed of a thermoplastic material, an inside liner and an outside sheathing, said blank forming a receiving space for receiving a shank stump and having a receiving opening restricted by an edge of said side wall, for inserting said shank stump, wherein, for the purpose of adapting the height of said edge of said blank to said shank stump to be received, a slit-shaped recess is arranged in said side wall and runs along said edge and extends from said edge into said side wall by a predetermined depth (T), and wherein the slit-shaped recess is arranged in the center of the side wall such that a double wall portion is formed with an inner wall adjacent to the inner liner and an outer wall adjacent to the outer sheathing, whereby the thickness of the inner wall essentially corresponds to the thickness of the outer wall.

9. A blank for producing a soft wall inside socket of a prosthesis comprising a pre-shaped side wall having a thickness (D) and being formed of a thermoplastic material, an inside liner and an outside sheathing, said blank forming a receiving space for receiving a shank stump and having a receiving opening restricted by an edge of said side wall, for inserting said shank stump, wherein, for the purpose of adapting the height of said edge of said blank to said shank stump to be received, a slit-shaped recess is arranged in said side wall and runs along said edge and extends from said edge into said side wall by a predetermined depth (T), and wherein the depth (T) of the slit-shaped recess is about 2 to 4 cm and the width (B) of said slit-shaped recess is about ⅓ to ½ of the thickness (D) of the side wall.

\* \* \* \* \*